United States Patent [19]

Kohnert et al.

[11] Patent Number: 5,723,122
[45] Date of Patent: Mar. 3, 1998

[54] USE OF THE PROTEASE DOMAIN OF HUMAN PLASMINOGEN ACTIVATOR FOR THE TREATMENT OF THROMBOEMBOLIC DISEASES

[75] Inventors: Ulrich Kohnert, Habach; Anne Stern, Penzberg; Ulrich Martin, Mannheim; Stephan Fischer, Polling, all of Germany

[73] Assignee: Boehringer Mannheim GmbH, Penzberg, Germany

[21] Appl. No.: 456,566

[22] Filed: Jun. 1, 1995

[51] Int. Cl.$^6$ .................. A61K 38/43; A61K 38/48; C12N 9/48; C12N 9/70
[52] U.S. Cl. .................. 424/94.1; 424/94.64; 435/216; 435/217; 435/219
[58] Field of Search .................. 435/212, 216, 435/217, 219; 424/94.1, 94.64

[56] References Cited

U.S. PATENT DOCUMENTS

| | | | |
|---|---|---|---|
| 5,223,256 | 6/1993 | Stern et al. | 424/94.63 |
| 5,242,688 | 9/1993 | Burck et al. | 424/94.64 |

OTHER PUBLICATIONS

Burck et al., "Characterization of a Modified Human Tissue–Plasminogen Activator Comprising a Kringe–2 and a Protease Domain", J. Biol. Chem. 265 (9): 5170–5177 (1990).
Robinson et al., "Redesigning t–PA for improved thrombolytic–therapy", Trends Biotech. 9 (3): 86–90 (1991).
Gething et la., "Variants of Human Tissue Type Plasminogen–Activator That Lack Specific Structural Domains of the Heavy Chain", EMBO J 7(9): 2731–2740 (1988).
Stockinger et al., 1992, Thrombosis Res., vol. 67, pp. 589–599.
Konnert et al., 1992, Protein Eng., vol. 5, No. 1, pp. 93–100.

Primary Examiner—Marian C. Knode
Assistant Examiner—Ali R. Salimi
Attorney, Agent, or Firm—Felfe & Lynch

[57] ABSTRACT

The invention relates to the use of thromboembolic proteins. These contain, as their only structural portion effecting thrombolytic activity, the protease domain of human tissue type plasminogen activator. These derivatives show reduced side effects, such as a reduction in bleeding while, demonstrating remarkable in vivo efficacy. The effect is surprising, given their in vitro properties.

19 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CAGAATTCTT ATGTCTTACC AATCCACCTG CGGCCTGAGA CAG    43

USE OF THE PROTEASE DOMAIN OF HUMAN PLASMINOGEN ACTIVATOR FOR THE TREATMENT OF THROMBOEMBOLIC DISEASES

FIELD OF THE INVENTION

The invention is concerned with the use of the protease domain of human plasminogen activator, medicaments for the treatment of thromboembolic diseases, pharmaceutical compositions which contain, as an active component, said protein, and the uses thereof.

BACKGROUND AND PRIOR ART

Tissue-type plasminogen activator (t-PA) is a serine protease consisting of several domains, which catalyzes the conversion of plasminogen to plasmin and is employed for fibrinolytic therapy.

A large number of t-PA variants and mutations are known, as will be seen for instance, by review of articles by T. J. R. Harris, Prof. Eng. 1: 449–459 (1987) and J. Krause, Fibrinolysis 2: 133–142 (1988).

It is known, inter alia, that fibrinolysis is regulated partly by the interaction between t-PA and the plasminogen activator inhibitor 1 (PAI-1), a serine protease inhibitor from the serpine family. The binding of PAI-1 to t-PA is essentially accomplished via amino acids 296–302 of t-PA. Mutation of this region causes a reduction of the inhibitory influence of PAI-1 on t-PA (E. L. Madison et al. (1990)). Extensive investigations have been carried out on the mechanism of the interaction between amino acid region 296–302 of t-PA and PAI-1 (cf. E. L. Madison, Nature 339 (1989) 721–723, R. V. Schohet, Thrombosis and Haemostasis 71 (1994) 124–128, C. J. Refino, Thrombosis and Haemostasis 70 (1993) 313–319, N. F. Paoni, Protein Engineering 6 (1993) 529–534 and Thrombosis and Haemostasis 70 (1993) 307–312, W. F. Bennett, J. Biol. Chem. 266 (1991) 5191–5201, D. Eastman, Biochemistry 31 (1992) 419–422.

Unmodified t-PA, in its form as occurs in plasma (i.e., "wild type" t-PA), consists of 527 amino acids, and can be split by plasmin into two chains which are then still held together via a disulfide bridge. The A chain (also referred to as the heavy chain) consists of four structural domains. The finger domain (amino acids 1–49) displays certain similarities to the finger structures in fibronectin. The growth factor domain (amino acids 50–86), is to a certain extent, homologous to murine and human epidermal growth factors. The two kringle domains (amino acids 87–175 and 176–262) are to a large extent homologous to the fourth and fifth kringle domain of plasminogen. The finger domain and the kringle 2 domains of t-PA are especially involved in fibrin binding and in the stimulation of proteolytic activity by fibrin. The B chain of t-PA (amino acids 276–527, protease domain) is a serine protease and is largely homologous to the B chains of urokinase and plasmin (T. J. R. Harris, supra and J. Krause, supra). t-PA variants which exhibit lower bleeding side effects are described in WO 93/24635 and by B. A. Keyt et al., PNAS USA 91: 3670–3674 (1994). These t-PA variants have an additional glycosylation site at amino acid positions 103–105. In addition, these t-PA variants may be modified at amino acids 296–302, whereby fibrin specificity is increased.

The object of the present invention is to provide thrombolytically active proteins which, have, inter alia lower bleeding side effects as compared to the known plasminogen activators.

DETAILED DESCRIPTION OF PREFERRED EMBODIMENT

Figure 1:
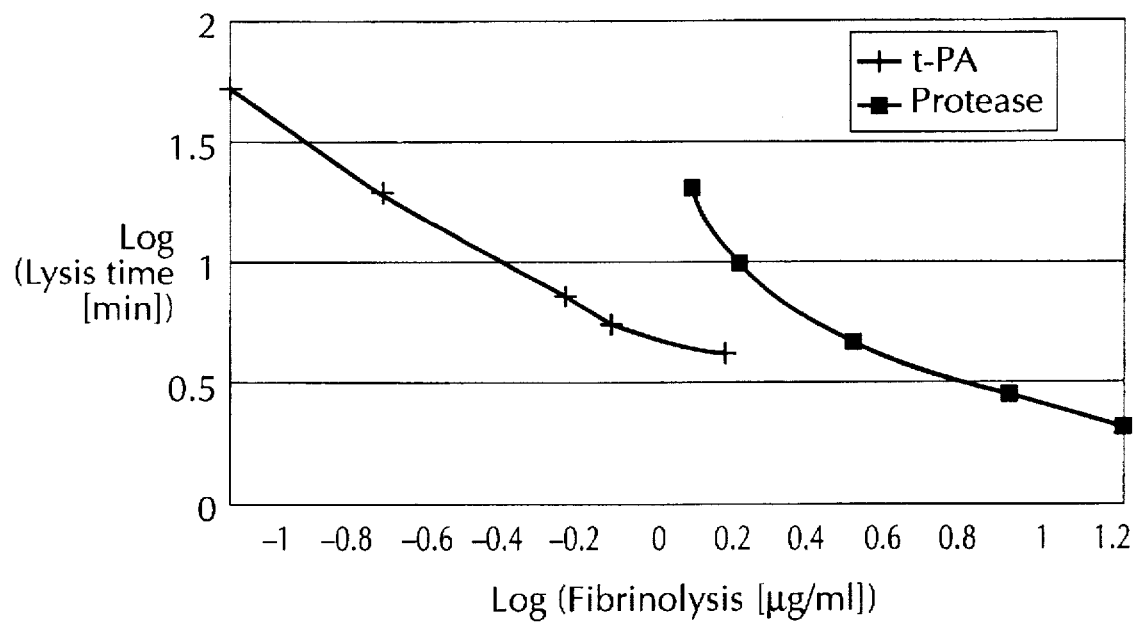
FIG. 1 presents a comparison of clot lysis activity of recombinant, wild type human tissue type plasminogen activator ("t-PA"), and a thrombolytically active protein in accordance with the invention, consisting of amino acids 1–3 and 262–527 of wild type t-PA.

The object of the invention is accomplished via a thrombolytically active protein and medicaments based upon it which are used for the treatment of thromboembolic diseases, wherein the protein contains, as the only structure effecting thrombolytic activity, the protease domain of human tissue-type plasminogen activator (i.e., amino acids 262–527, as set forth supra). Preferably, the protein consists of the essential parts of the protease domain. The proteins have plasminogenolytic activity less than about 25 KU/mg, more preferably less than about 10 KU/mg, and most preferably less than about 2.5 KU/mg, where KU is kilo units.

By the essential parts of the domain there are to be understood those amino acid regions which are required for the protease portion of the biological effectiveness of the plasminogen activator. With reference to the amino acid sequence of wild type human tissue plasminogen activator as set forth in Goeddel, et al., U.S. Pat. No. 4,766,075 incorporated by reference, amino acids Ile$_{276}$ to C terminal end (position 527) are required, at a minimum. The N-terminus may, however, begin with any amino acids beginning with Ser$_{262}$ of wild type t-PA up to Ile$_{276}$. Preferably, the N-terminus starts with Ser$_{264}$, Cys$_{262}$, or Ile$_{276}$ and the C-terminus is 527. Preferred modifications are well known in the art, as will be seen by review of , e.g., PCT Application WO93/24635, Paoni, et al., Thromb. & Harmostas. 70: 307–312 (1993); Paoni, et al., Prof. Engineering 6: 529–534 (1993); Shohet et al., Thromb. & Hemostas. 71: 124–128 (1994); Madison et al., Nature 329: 721–723 (1989); Madison et al., Proc. Natl. Acad. Sci. USA 87: 3530–3533 (1990); Madison, et al., Proc. Natl. Acad. Sci. USA 91: 3670–3674 (1994); and German Patent Application 4423574.7, the disclosures of which are all incorporated by reference. Also preferred are thrombolytically active proteins containing alterations within amino acids 296–302, and/or 274–277 of wild type t-PA. Especially preferred is the substitution of all of amino acids 296–299 by alanine, and/or replacement of the amino acids at positions 274–277 by one or more of leucine, histidine, serine, and threonine. Further preferred modifications are set forth in the abstract of Chero et al., Thromb. & Haemostas. 69: 762 (1993) (Abstract 794), describing substitutions at position 276, 364–366, 432, 434, 460, 462 and 466–470. These modifications, as set forth in these references, are all incorporated by reference. Cys$_{264}$ is desirably included because it forms a cysteine-cysteine bond with Cys$_{395}$, thus stabilizing three dimensional structure. The N-terminus may also begin with any of amino acids Gly$_{-3}$ up through Ile$_5$, preferably any of amino acids Ser$_1$, through Gln$_3$, followed immediately by one of the N-terminus options presented supra. See Harris, Prof. Eng. 1: 449–458 (1987), incorporated by reference. These options correspond to amino acids encoded by nucleotides positioned in the region of the human t-PA DNA before the intron/exon junction of the fibrin finger. Similarly, with reference to amino acids Ser$_{262}$ to Ile$_{276}$, Ser$_{262}$ is positioned at an intron/exon junction. Within these constraints, minor modifications such as substitutions, deletions, additions, and/or modifications of one or more amino acids are possible, as long as the proteolytic character of the molecule is not changed. $Ser_{262}$ is especially preferred as the N-terminus of the molecule. Proteolytic activity can be determined very easily, using any of the well known assays for determining this property, including those set forth herein.

Thrombolytically active proteins in accordance with the invention exhibit low fibrin binding and very low plasminogenolytic activity in vitro (determined according to Verheijen, J. et al., Thromb. Haemostas. 48: 266–269 (1982)) and have therefore not been considered as suitable thrombolytic therapeutic agents up to now. The properties of these proteins include plasminogenolytic activity less than about 2.5 KU/mg, and less than about 10% of fibrin binding activity of wild type human tissue type plasminogen activator. These molecules are also not stimulated by CNBr fragments of fibrinogen. Surprisingly, a distinctly reduced risk of bleeding compared to known plasminogen activators and high activity are found, however, when they are used in vivo.

The fibrin binding protein in accordance with the invention can be determined in a fibrin binding test, wherein thrombin at a final concentration of 2.5 NIH units/ml is added to a solution of the protease and 1.2 mg/ml fibrinogen in buffer solution (Veronal® 15 mmol/l, NaCl 28 mmol/l, $CaCl_2$ 0.5 mmol/l, $MgCl_2$ 0.2 mmol/l, Tris HCl 5 mmol/l and 0.005% (v/v) Tween® 80, pH 7.75). After three minutes at 25° C. the resulting fibrin clots are removed by centrifugation at 12,000xg for 8 minutes and the amount of the thrombolytically active protein retained in the supernatant is determined photometrically. The method set forth in example 5, infra, can also be used to determine fibrin binding. Indeed, this is the preferred method.

In a rabbit model of jugular vein thrombolysis, as taught by J. Clin. Invest. 71: 368–376 (1993), the proteins in accordance with the invention, at a dosage of 1 mg/kg of protein, display at least 50% lower blood loss compared to human tissue-type plasminogen activator, when a radioactively labeled thrombus is formed in the jugular vein. 100 IU/kg of heparin are administered subcutaneously, and a single intravenous bolus injection of 1 mg/kg protein is given and the bleeding is determined according to J. Clin. Invest. 71: 368–376 (1993).

It is thus possible, by using the thrombolytically active proteins of the invention, to retain a therapeutically relevant thrombolytic effect and to reduce the bleeding side effects observed clinically, by more than 50%. This property is not lost even when the dose of protein is increased.

The thrombolytically active proteins of the invention, unlike wild type t-PA, are suitable for use as intravenous bolus injections. One may attain practically the same thrombolytic effect as the customary infusion of wild type t-PA, using lower doses of the protease. Surprisingly, therapy using protease results in less than 50% of the blood loss found when using wild type t-PA. This property is highly significant with respect to the safety profile of thrombolytically active proteins, since it reduces the side effect of bleeding which otherwise usually occurs in the case of thrombolytic agents, such as wild type t-PA. Data relating to the measurement of activated partial thrombin time or "aPTT" furthermore suggests that the proteins of the invention, at an effective dose, do not split the proteins required for normal coagulation, as the aPTT values were very comparable between the groups. In the case of higher doses, the fibrinogen-saving effect may be lost; however, this would not affect the reduction of the side effects. On the contrary, the reduction of blood loss is not related to the fibrin specificity nor is it linked to the dosage.

The lowering of the bleeding side effects makes the proteins of the invention exceedingly valuable thrombolytic agents for the treatment of all thromboembolic diseases. In contrast to the thrombolytic agents that have hitherto been approved only for diseases which pose a very great danger to life, such as cardiac infarction and massive pulmonary embolism, one may use the inventive proteins in less acutely life-threatening diseases, such as, e.g., deep vein thrombosis of the leg. In addition to this, thrombolytic agents based on the use of the protease domain as the sole, thrombolytically active domain can now be applied in a much wider range than before, since the prior danger of bleeding complications is no longer an issue. Irrespective of this, the inventive proteins can also be used advantageously for acute diseases, such as cardiac infarction or pulmonary embolism.

The preparation of the thrombolytically active proteins in accordance with the invention can be carried out in eukaryotic or prokaryotic cells according to the methods known to one skilled in the art. Preferably, the compounds according to the invention are prepared by genetic engineering techniques. Such methods are described, for example, in WO 90/09437, EP-A 0 297 066, EP-A 0 302 456, EP-A 0 245 100 and EP-A 0 400 545 all of which are incorporated herein by reference with regard to such methods of production. Mutations can be inserted into the cDNA of t-PA or a derivative thereof by means of oligonucleotide-directed site-specific mutagenesis. Site-specific mutagenesis is described, for instance, by Zoller and Smith, DNA 3: 479–488 (1984), modified according to T. A. Kunkel, PNAS 82: 488–492 (1985) and Morinaga et al., Biotechnology 21: 634 (1984). The method of PCR mutagenesis which is described, for example, in Ausubel et al., Current Protocols In Molecular Biology, Vol. 2, Chapter 15 (Greene Publ. Associates & Wiley Interscience 1991) is also suitable. These methods are also incorporated by reference.

The nucleic acid molecules obtained in this way serve the expression of the t-PA derivative employed according to the invention, especially if it is present on an expression vector suitable for the host cell used.

The nucleic acid molecules which code for proteins according to the invention can also be modified. Examples of such modifications include:

changing the nucleotide sequence so as to introduce different recognition sequences of restriction enzymes in order to facilitate the steps of ligation, cloning and mutagenesis;

changing the nucleotide sequence so as to incorporate preferred codons for the host cell;

supplementing the nucleotide sequence with additional regulatory and transcription elements so as to optimize expression in the host cell.

All of the other process steps for the preparation of appropriate expression vectors and for the expression are state of the art and are well-known to one skilled in the art. Such methods are described, for instance, in Sambrook et al., Molecular Cloning: A Laboratory Manual (Cold Spring Harbor, 1989).

The preparation of glycosylated proteins employed according to the invention is carried out in eukaryotic host cells. The preparation of non-glycosylated proteins according to the invention may be carried out in either eukaryotic host cells, wherein the resulting glycosylated product must be deglycosylated by methods known to one skilled in the art, or, preferably, by expression in non-glycosylating host cells, more preferably in prokaryotic host cells.

Suitable prokaryotic host organisms include *E.coli, Streptomyces spec.* or *Bacillus subtilis*. To prepare the proteins according to the invention, the prokaryotic cells are cultivated in the usual manner and, after digestion of the bacteria, the protein is isolated in the usual manner. If the protein is obtained in inactive form (e.g. as inclusion bodies), it is solubilized and renatured according to the methods known to one skilled in the art. According to these, it is also possible to secrete the protein from the microorganisms in the form of an active protein. An expression vector suitable for this purpose preferably contains a signal sequence appropriate for the secretion of proteins in the employed host cells, and the nucleotide sequence coding for the protein. In this connection, the protein expressed by this vector is secreted either into the medium (in the case of gram-positive bacteria) or into the periplasmatic region (in the case of gram-negative bacteria). It is preferred to employ a sequence coding for a cleavage site between the signal sequence and the sequence coding for the proteins of the invention, which allows the splitting off of the protein either during processing or by treatment with protease.

The selection of the base vector into which the nucleic acid molecule coding for the protein of the invention is inserted is dependent upon the host cells that are used for expression. The skilled artisan is aware of appropriate plasmids as well as of the minimum requirements to be met by a plasmid of this type (e.g. replication origin, restriction cleavage sites). Instead of a plasmid, a cosmid, the replicative double-stranded form of phages (λ, M13), or other vectors known to one skilled in the art can be used within the framework of the invention.

In preparing the proteins according to the invention in prokaryotes which do not secrete them, it is preferred to separate the resulting inclusion bodies from the soluble cell particles, solubilize the inclusion bodies by treatment with denaturing agents under reductive conditions, subsequently derivatize with glutathione disulphide, i.e., GSSG and renature the protein by adding glutathione, i.e. GSH and denaturing agents at a non-denaturing concentration, or by adding L-arginine. Such methods for the folding and/or activation of proteins and derivatives from inclusion bodies are described, for example, in EP-A 0 219 874 and EP-A 0 241 022. Other methods of recovering the active protein from the inclusion bodies can be applied as well.

Preferably, purification of the proteins according to the invention is carried out in the presence of L-arginine, in particular at an arginine concentration of from about 10 to about 1000 mmol/l. The separation of foreign proteins is performed, preferably, by means of affinity chromatography, and more preferably via an adsorber column on which ETI (Erythrina trypsin inhibitor) is immobilized. As carrier material, Sepharose®, e.g., may be used. Purification via an ETI adsorbtion column offers the advantage that the ETI adsorbtion column material can be loaded directly from the concentrated renaturation batch even in the presence of arginine concentrations as high as 0.8 mol/l arginine. Preferably, purification of the thrombolytically active proteins according to the invention is carried out via an ETI adsorbtion column in the presence of 0.6 to 0.8 mol/l arginine. The solution applied to the column preferably has a pH higher than 7, more preferably between 7.5 and 8.6.

Elution from the ETI column of the proteins of the invention is accomplished by lowering the pH both in the presence and in the absence of arginine under conditions at which the proteins of the invention are readily soluble. In this, the pH value is preferably within the acidic range, preferably between about pH 4.0 and pH 6.5 more preferably between pH 4.0 and 5.5.

Another aspect of the invention is a pharmaceutical composition containing a thrombolytically active protein, wherein the protein contains as the only structure effecting thrombolytic activity the protease domain of human tissue-type plasminogen activator.

The proteins of the invention can be formulated, in a manner known to one skilled in the art, in therapeutic agents, wherein the compounds according to the invention usually are combined with a pharmaceutically acceptable carrier. Typically, such compositions contain as a dose an effective amount of 0.3 to 7 mg/kg, preferably 0.7 to 5 mg/kg, and more preferably 1 to 3 mg/kg body weight. The therapeutic compositions usually are present as sterile aqueous solutions or as sterile, soluble dry formulations, such as lyophilisates. The compositions usually contain an appropriate amount of a pharmaceutically acceptable salt with which an isotonic solution is prepared. Further, buffers such as arginine buffer or phosphate buffer, can be applied to stabilize the compositions at an appropriate pH value (preferably 5.5 to 7.5). The dosage level of the compounds according to the invention can be easily determined by a person skilled in the art. Relevant factors include, e.g., the mode of application (infusion or bolus) and the duration of therapy. Due to their extended half-life the compounds according to the invention are particularly useful for bolus application (single bolus, multiple bolus). For instance, an ampoule containing 25 to 1000 mg of a compound according to the invention, arginine, and a buffer may be used in bolus application. Application is preferably performed intravenously, but may also be accomplished subcutaneously, intramuscularly or intra-arterially. The protein can also be infused or applied locally.

The compounds according to the invention can be applied as a multiple bolus (preferably as a double bolus). Appropriate time intervals for multiple boli are between 20 and 180 minutes, an interval between 30 and 90 minutes being more preferred and an interval between 30 and 60 minutes being most preferred. It has been found, however, that, surprisingly, the proteins are sufficiently effective in single bolus application. In this connection, the dosage preferably is about 1 mg/kg of body weight.

The compounds according to the invention are useful, in particular, for the treatment of all thromboembolic diseases such as, e.g., acute cardiac infarction, cerebral infarction, pulmonary embolism, deep vein thrombosis of the leg, acute arterial occlusion, etc. More preferably, the compounds according to the invention are applied for treating subchronic thrombo-embolic diseases where thrombolysis must be carried out for an extended period of time.

It is preferred to apply the compounds according to the invention in combination with a substance inhibiting coagulation (anticoagulant) such as heparin or hirudin, and/or a substance inhibiting platelet aggregation, whereby the vessel-opening effect is enhanced with little side effects being involved. It is also preferred to add substances stimulating the blood flow or substances which improve microcirculation.

The following examples are provided to aid the understanding of the present invention, the true scope of which is set forth in the appended claims. It is understood that modifications can be made in the procedures set forth without departing from the spirit of the invention.

EXAMPLE 1

Expression in *E.coli* a) Construction of the expression plasmid

The starting plasmid pA27fd, described in EP 0 382 174 and incorporated by reference, contains the following components: tac promoter, lac operator region with an ATG starting codon, the coding region for a t-PA derivative consisting of the kringle-2 domain and the protease domain (amino acids 1-3 and 176-527), and the fd transcription terminator. Plasmid pKK223-3 is the starting vector.

For the deletion of the sequence coding for the kringle-2 domain (deletion of amino acid positions 176-261; in accordance with Pennica et al., 1983, Nature 301: 214) incorporated by reference), the method of Morinaga et al. (1984, Biotechnology 21: 634) was essentially carried out. For mutagenesis, oligonucleotide SEQ ID NO: 1 was prepared synthetically.

The formation of the heteroduplex was performed as described in EP 0 382 174, incorporated by reference. The heteroduplex preparation together with the plasmid pUBS520 (Brinkmann et al., 1989, Gene 85:109) was transformed in E.coli C600+. The transformants were selected by adding to the nutrient medium ampicillin and kanamycin (50 µg/ml each). The resulting plasmid was called pA27Protease; it is distinguished from the starting plasmid by the absence of an EcoRI cleavage site.

b) Expression in E. coli

To examine expression, the E.coli strain C600+ was cultured with the plasmids pA27Protease and pUBS520 in LB medium (Sambrook et al., supra) in the presence of ampicillin and kanamycin (50 µg/ml each) until an OD at 550 nm of 0.4 was attained. The expression was initiated by adding 5 mmol/l IPTG. The culture was incubated for a further four hours. Subsequent to this, the E.coli cells were collected by centrifugation and resuspended in buffer (50 mmol/l Tris HCl pH 8, 50 mmol/l EDTA); lysis of the cells was brought about by sonication. Following an additional step, i.e., centrifugation, the insoluble protein fractions were collected and resuspended in the above-mentioned buffer by sonication. The suspension was mixed with ¼ volume of loading buffer (250 mmol/l Tris HCl pH 6.8, 10 mmol/ EDTA, 5% SDS, 5% mercaptoethanol, 50% glycerol and 0.005% bromophenol blue) and analyzed with the aid of a 12.5% SDS polyacrylamide gel. As a control, the same preparation was carried out using a culture of E.coli with the two above-mentioned plasmids which had not been induced with IPTG, and separated in the gel. In the preparation of the IPTG-induced culture, after staining the gel with Coomassie Blue R250 (dissolved in 30% methanol and 10% acetic acid), one can see a distinct band having a molecular weight of about 30 kD. This band is not present in the control preparation.

1983; 71: 368–376 incorporated by reference) was applied. In this, a radioactively labeled thrombus was formed in the jugular vein in the animals. The animals were anticoagulated subcutaneously, using 100 IU/kg heparin. Alteplase (recombinant, wild type tissue-type plasminogen activator "t-PA", commercially available as Actilyse® from the company Thomae, Biberach, Germany), the protein described in Example 1, streptokinase (commercially available as Streptase® from Behring, Marburg, Germany) or solvent (0.2 M arginine phosphate buffer) were administered to the rabbits intravenously.

The placebo group was given an intravenous single bolus injection of 1 ml/kg solvent. The Alteplase group was given, intravenously, a total dose of 1.45 mg/kg, of which 0.2 mg/kg were in the form of a starting bolus injection, 0.75 mg/kg in the form of a 30 minutes' infusion, immediately followed by 0.5 mg/kg as a 60 minutes' continuous infusion (total infusion: 90 min.). The streptokinase group was given a 60 minutes' intravenous infusion of 64,000 IU/kg. The protease group was given an intravenous single bolus injection of 1 mg/kg or 2 mg/kg. For Alteplase and streptokinase, these are accepted, standard regimes.

Two hours after the start of therapy, any thrombus remaining was removed, and the extent of the dissolution of the thrombus (thrombolysis) was determined by means of the decrease of radioactivity in the thrombus. Blood samples for obtaining plasma were taken prior to therapy and 2 hours after the start of therapy for use in recovering plasma. Activated partial thromboplastin time was measured, using a standard method. Furthermore, any blood loss caused by the thrombolytic therapy, was quantified. To this end, prior to the administration of the thrombolytic agents, a defined skin incision (4 cm in length and 0.3 cm in depth) was made on the thigh of the animals using a template and a scalpel. The bleeding which occurred as a result stopped as a result of natural coagulation. After the start of therapy, a sponge was placed on the wound, soaking up the blood from the bleeding which had newly started as a result of the thrombolysis. By weighing the sponge (after subtracting the sponge's own weight), the amount of blood issuing from the wound was measured and in this way specified the extent of the bleeding side effect.

Results:

A summary of the results is shown in table 1 below:

TABLE 1

| substance | dose | infusion or injection | thrombolysis (%) | aPTT-extension (%) | blood loss (mg) |
|---|---|---|---|---|---|
| solvent | 1 ml/kg | i.v injection | 11.5 ± 2.1 | 117 ± 4 | 58 ± 11 |
| alteplase | 1.45 mg/kg | i.v. infusion | 62.1 ± 12.9* | 120 ± 5 | 4195 ± 1400* |
| streptokinase | 64000 IU/kg | i.v. infusion | 74.4 ± 9.5* | 122 ± 5 | 10434 ± 5608* |
| protease | 1 mg/kg | i.v. injection | 46.7 ± 8.9* | 125 ± 5 | 1961 ± 473* |
|  | 2 mg/kg# | i.v. injection | 53.9 ± 7.6 | 283 ± 89 | 1197 ± 442* |

Mean value of 6 experiments per group ± SEM; * p < 0.05 (t test) vs. solvent, #n = 4.

EXAMPLE 2

In vivo characterization of the protease of t-PA

To examine thrombolytic potency and efficiency of the proteins of the invention, the rabbit model of jugular vein thrombolysis established by D. Collen (J. Clin. Invest., Both Alteplase and the protease of the invention are highly active thrombolytic substances and, compared to the solvent control both significantly dissolved the thrombi. However, a dose of 1 mg/kg (invention) instead of 1.45 mg/kg of (Alteplase), i.e., a 31% lower dose, was effective. The dose and mode of administration (three-stage infusion)

used for Alteplase corresponds to the dose and mode of administration customarily applied in the clinic when treating cardiac infarction (see GUSTO study: N. Engl. J. Med., 1993; 329: 673–82). The fact that a lower dose can be used to achieve a therapeutically relevant effect, viz the dissolution of thrombi, which is advantageous, and also the ability to achieve this effect with a single bolus injection, distinguish the invention from other thrombolytically active agent, including Alteplase. The results cannot be achieved using Alteplase.

It is extremely important, however, to note that it was surprisingly observed that carrying out a method involving 1 mg/kg of the invention the loss of blood was only half as much (46.8%) at most, as compared to Alteplase. A 71% lower blood loss occurred at the higher protease dose of 2 mg/kg, as compared to the standard therapy with Alteplase. Compared to streptokinase, this difference is even more distinct. It is particularly noteworthy that the blood loss in the case of alteplase and streptokinase occurs without the aPTT being markedly extended, which suggests that no remarkable fibrinogen splitting has taken place in vivo. In contrast, aPTT extension is indeed to be found in the case of the higher dose of the protein of the invention, this having however no negative influence whatsoever on the bleeding tendency.

EXAMPLE 3

Comparison of the clot lysis activity of t-PA and recombinant protease t-PA and recombinant protease were adjusted with buffer to the concentrations given in FIG. 1 and their activity was determined in the clot lysis assay.

Carrying out the clot lysis assay

The sample is adjusted to the protein concentration required in the particular case by adding buffer (0.06 M $Na_2HPO_4$, pH 7.4, 5 mg/ml BSA (bovine serum albumin), 0.01% Tween®). 0.1 ml of the sample were mixed with 1 ml human fibrinogen solution (IMCO) (2 mg/ml 0.006 M $Na_2HPO_4$, pH 7.4, 0.5 mg/ml BSA, 0.01% Tween 80®) and incubated at 37° C. for 5 minutes. Subsequently, 100 µl, in each case, of a plasminogen solution (10 IU/ml 0.06 M $Na_2HPO_4/H_3PO_4$, pH 7.4, 0.5 mg/ml BSA, 0.01% Tween 80°) and of a thrombin solution (30 U/ml 0.06 M $Na_2HPO_4$, pH 7.4, 0.5 mg/ml BSA, 0.01% Tween 80®) were added and the test preparation is again incubated at 37° C. After 2 minutes, a Teflon® ball is placed on the fibrin clot and the time required for the ball to reach the bottom of the test tube is measured.

EXAMPLE 4

This example tests the thrombolytically active protein of Example 1 for its ability to bind to fibrin, and also compares it to recombinant, human tissue type plasminogen activator for this property.

Actilyse® is recombinant human tissue type plasminogen activator produced in Chinese Hamster Ovary (CHO) cells. Samples of Actilyse, and a protein in accordance with the invention, were prepared as solutions of 1.5 ug protein/ml. Samples (100 ul) of each thrombolytically active protein were then mixed with 770 ul buffer (0.05M Tris/HCl, pH 7.4, 0.15 NaCl, 0.01% Tween 80) 10 ul bovine serum albumin solution (100 mg/ml), 10 ul aprotinin (3.75 mg/ml), 10 ul bovine thrombin (concentration 100 U/ml) and increasing amounts of fibrinogen. Note that the amount of fibrin present ranged from 10 ug/ml to 300 ug/ml. All solutions were aqueous. The total amount of fibrinogen present was 100 ug/ml of solution. It is well known that thrombin converts fibrinogen to an insoluble fibrin clot.

The components were mixed, and incubated for one hour at 37° C. Subsequently, supernatant was separated from the fibrin clot via centrifugation (15 minutes, 13,000 RPM, at 4° C.), and the amount of thrombolytically active protein present in the supernatant was determined via a standard ELISA.

Figure 2:
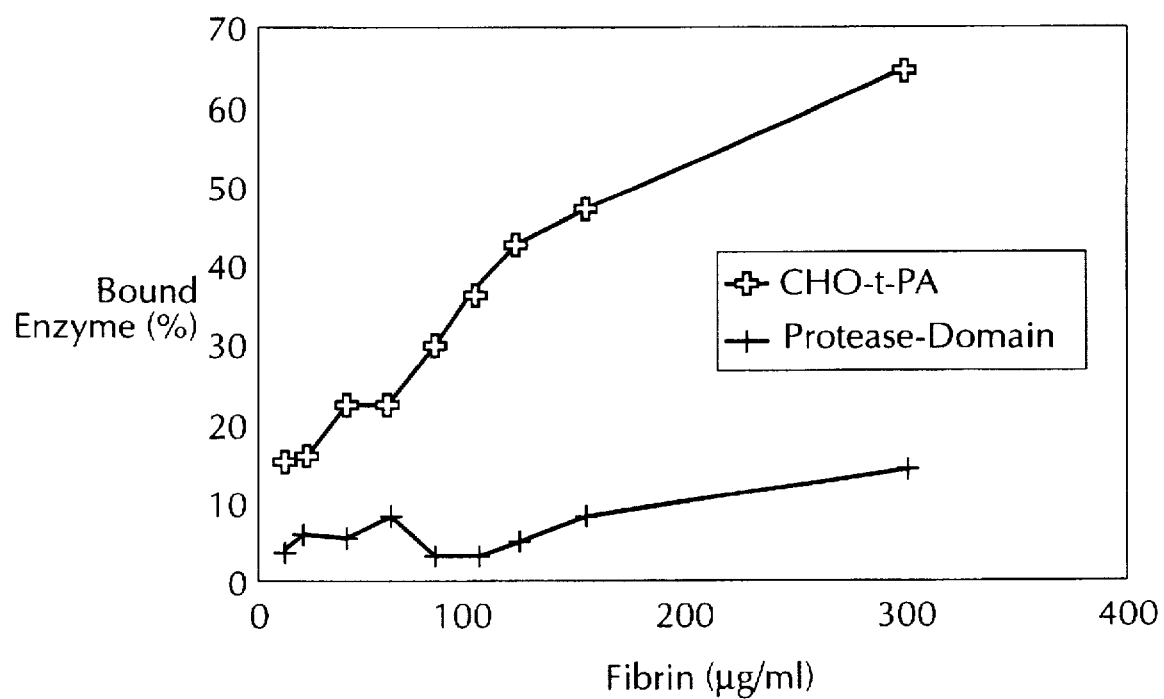
FIG. 2 compares fibrin binding of recombinant human tissue type plasminogen activator to a thrombolytically active protein in accordance with the invention (a protein containing amino acids 1–3 and 262–527 of wild type t-PA), over various concentrations of fibrin.

The results are set forth in FIG. 2. The amount of recombinant t-PA which bound to the fibrin clot ranged from 15% (10 ug/ml fibrin), up to 65%, at 300 ug/ml. In contrast, the thrombolytically active protein showed insignificant binding at low concentrations, and only rose to about 10% at the top of the range. This low value can be attributed to non-specific inclusion of the protein in the fibrin net, rather than to specific binding between the protein and the clot.

It can be concluded, therefore, that thrombolytically active protein in accordance with the invention does not significantly bind to fibrin.

EXAMPLE 5

A well known methodology for determining plasminogenolytic activity is that described by Verheijen, et al., Thromb. Haemost. 48: 266–269 (1982), incorporated by reference, but discussed herein.

The reagents used in this assay include fibrinogen fragments, "Lys-plasminogen", and aprotinin-Eupergit. The first of these, which acts as a thrombolytically active protein stimulator, was prepared by treating human fibrinogen with cyanogen bromide (1 g human fibrinogen, 1.3 g CNBr in 100 ml water), in 70% v/v formic acid, for 17 hours at room temperature, followed by dialysis against distilled water.

Lys-plasminogen is human plasminogen which contains primarily lys-plg, which has been isolated from Cohn fraction III, via affinity chromatography on lysine sepharose, followed by treatment with aprotinin-Eupergit to remove plasmin.

To make aprotinin-Eupergit, 39 mg aprotinin were coupled to 4 g of Eupergit™C oxirane acrylic beads, following the manufacturer's instructions.

In the assay, 50 mU of Actilyse or the protein of Example 1 were incubated in 1 ml of 0.1 mol/l Tris/HCl (pH 7.5), containing 0.1% (v/v) Tween 80, 0.13 µmole/liter Lys-plasminogen, 0.3 mmol of substrate S2251 (chromogenic substrate H-D-Val-Leu-Lys-p nitroanilide.HCl), and 120 ug/ml fibrinogen fragments. The mixtures were incubated for two hours at 25° C., and the absorbance at 405 nm was measured against control blanks, without stopping the reaction. Cleavage of the chromogenic substrate S2251 is what is measured, which is a measure of the plasminogenolytic activity of the enzyme.

Actilyse was determined to have activity of from about 500 to about 700 KU/mg, as compared to the compound of the invention, with an activity of about 2.5 KU/mg. Thus, the invention has 1/200–1/300 the plasminogeneolytic activity of the recombinant t-PA. There was no stimulation of the compound of the invention by the fibrinogen fragments, as compared to the t-PA, which was stimulated by a factor of from 30–50.

Comparison of the specific plasminogenolytic activity of CHO t-PA and the protease domain of r-PA The plasminogenolytic activity was determined according to the method of Verheijen et al. (1982), Thromb. Haemost.

48, 266–269. The protein concentration was determined from the absorption at 280 nm with $E_{280}=1.81$ and 1.42 cm²/mg for CHO-t-PA and for the protease respectively.

The specific activity is the quotient for the plasminogenolytic activity (KU/ml) and the protein concentration (mg/ml).

TABLE 2

| Substance | Specific Activity (KU/mg) |
|---|---|
| CHO-t-PA | 500–700 |
| Protease | 2.5 |

The results shown in table 2 show that the specific plasminogenolytic activity of protease is lower than the activity of CHO-t-PA by the factor 200–300. The plasminogenolytic activity of protease cannot be stimulated by CNBr fragments of fibrinogen. CHO-t-PA is stimulated by CNBr fragments of fibrinogen by the factor 30–50.

The surprising superiority of this derivative can be seen from an indirect comparison to the derivative TNK, described by Benedict et al., J. Am. Coll. Cardiol. suppl. 314(A) (1994), incorporated by reference. This publication compared wild type t-PA, the derivative TNK, and a control. The results are set forth in Table 3, which follows. When a compound in accordance with the invention ("protease" in Table 4, following), was compared to wild type t-PA, and streptokinase, using the model of the foregoing example, blood loss reduced diamatically. See Table 4.

TABLE 3

TNK vs. t-PA
(Literature: Benedict et al., J. Am. Coll. Cardiol. (1994) Suppl. 314 A)

| Agent | Dose | Blood weight (mg) | Relative reduction of blood loss (%) as compared to t-PA |
|---|---|---|---|
| t-PA | 9 mg/kg (120 min) | 65 ± 4.3 | — |
| TNK | 1.5 mg/kg (bolus) | 52 ± 4.8 | –20% |
| Control | — | 35 ± 6.2 | |

TABLE 4

Protease vs. t-PA according to example 2

| Agent | Dose | Blood weight (mg) | Relative reduction of blood loss (%) as compared to t-PA |
|---|---|---|---|
| Protease | 1 mg/kg (bolus) | 1961 ± 473 | –53% |
|  | 2 mg/kg (bolus) | 1197 ± 442 | –71% |
| t-PA | 1.45 mg/kg (90 min) | 4195 ± 1400 | — |
| Streptokinase | 64,000 IU/kg (60 min) | 10,434 ± 5608 | +149% |
| Control |  | 58 ± 11 | |

We claim:

1. Method for treating a thromboembolic condition comprising administering to a subject in need thereof a thrombolytically effective amount of an active molecule which is not stimulated by CNBr fragments of fibrinogen, has plasminogenolytic activity less than 25 KU/mg, is a protein or glycoprotein has less than 10% of the fibrin binding activity of wild type human tissue plasminogen activator, and an amino acid sequence which consists of no more than amino acids 262–527 of human wild type tissue plasminogen activator and no less than amino acids 276–527 of human wild type tissue plasminogen activator.

2. The method of claim 1, wherein said thrombolytically active molecule has plasminogenolytic activity less than 10 KU/mg.

3. The method of claim 1, wherein said thrombolytically active molecule has plasminogenolytic activity less than 2.5 KU/mg.

4. Method for treating a thromboembolic condition comprising administering to a subject in need thereof a thrombolytically effective amount of an active molecule, wherein said thrombolytically active molecule is a protein which consists of an amino acid sequence which consists of (i) no more than amino acids 1–3 of wild type human tissue plasminogen activator, concatenated to no more than amino acids 262–527 of human wild type tissue plasminogen activator or (ii) no more than amino acids 262–527 of human wild type tissue plasminogen activator.

5. The method of claim 1, wherein said thrombolytically active molecule is a glycoprotein, the protein portion of which consists of amino acids 1-3 of wild type human tissue type plasminogen activator at its N terminus, followed by amino acids 262-527 of human wild type tissue plasminogen activator.

6. The method of claim 1, wherein said thrombolytically active molecule is administered in a dose ranging from about 0.1 mg/kg to about 5 mg/kg of body weight of said subject.

7. The method of claim 1, wherein said thrombolytically active molecule is administered as a single bolus, a multiple bolus, intravenously, intramuscularly, subcutaneously, or intraaortically.

8. The method of claim 1, wherein said thrombolytically active molecule is administered via infusion or is applied locally.

9. The method of claim 1, wherein said thromboembolic condition is a deep vein thrombosis or an acute arterial occlusion.

10. Method for treating a thromboembolic condition, comprising administering to a subject in need thereof a thrombolytically active molecule which is a protein or glycoprotein, the protein portion of which consists of an amino acid sequence of which
  (i) has, at its N terminus, all or a portion of amino acids −3 through 5 of wild type human tissue type plasminogen activator, followed by
  (ii) all or a portion of amino acids 262 through 527 of wild type human tissue type plasminogen activator, with the proviso that said amino acid sequence contains at least amino acids 276 through 527.

11. The method of claim 10, wherein said thrombolytically active molecule contains amino acids 264 through 527 of human wild type tissue type plasminogen activator.

12. The method of claim 10, wherein said thrombolytically active molecule has, at its N terminus, amino acids 1-3 of wild type human tissue type plasminogen activator.

13. The method of claim 10, wherein (ii) of said thrombolytically active molecule consists of amino acids 276 to 527 of wild type human tissue type plasminogen activator.

14. Method for treating a thromboembolic condition, comprising administering to a subject a thrombolytically effective amount of an active molecule which is a protein or a glycoprotein, the protein portion of said molecule consisting of no more than amino acids 262 through 527 of wild type human tissue type plasminogen activator, and no less than amino acids 276 through 527 of wild type human tissue type plasminogen activator.

15. The method of claim 13, wherein the protein portion of said thrombolytically active molecule consists of amino acids 262 through 527 of wild type, human tissue type plasminogen activator.

16. The method of claim 13, wherein the protein portion of said thrombolytically active molecule consists of amino acids 264 through 527 of wild type, human tissue type plasminogen activator.

17. The method of claim 13, wherein the protein portion of said thrombolytically active molecule consists of amino acid 276 through 527 to wild type, human tissue type plasminogen activator.

18. Thrombolytically active molecule which is a protein or a glycoprotein, wherein the protein portion of said molecule consists of amino acids 1-3 and 262-527 of wild type, human tissue type plasminogen activator.

19. Composition useful in treating a thromboembolic condition comprising the thrombolytically active molecule of claim 18 and a pharmaceutically acceptable carrier.

* * * * *

UNITED STATES PATENT AND TRADEMARK OFFICE
CERTIFICATE OF CORRECTION

PATENT NO. : 5,723,122
DATED : March 3, 1998
INVENTOR(S) : Kohnert, et al.

It is certified that error appears in the above-identified patent and that said Letters Patent is hereby corrected as shown below:

In <u>column 2, line 34,</u> change "$Ser_{264}$" to -- $Ser_{262}$ --.
In <u>column 2, line 34,</u> change "$cys_{262}$" to -- $Cys_{264}$ --.
In <u>column 9, line 14,</u> change "at most" to -- <u>at most</u> --.

Signed and Sealed this

Fourth Day of July, 2000

Attest:

Q. TODD DICKINSON

Attesting Officer     *Director of Patents and Trademarks*